(12) United States Patent
Bohsung

(10) Patent No.: US 8,380,538 B2
(45) Date of Patent: Feb. 19, 2013

(54) FRACTION SEQUENCE CONCEPT FOR RADIATION THERAPY PLANNING

(75) Inventor: Joerg Bohsung, Heidelberg (DE)

(73) Assignee: Siemens Aktiengesellschaft, Munich (DE)

(*) Notice: Subject to any disclaimer, the term of this patent is extended or adjusted under 35 U.S.C. 154(b) by 978 days.

(21) Appl. No.: 12/056,673

(22) Filed: Mar. 27, 2008

(65) Prior Publication Data

US 2008/0240351 A1 Oct. 2, 2008

Related U.S. Application Data

(60) Provisional application No. 60/909,063, filed on Mar. 30, 2007.

(51) Int. Cl.
*G06Q 50/00* (2012.01)
(52) U.S. Cl. .................. 705/3; 705/2
(58) Field of Classification Search .................. 705/2–4
See application file for complete search history.

(56) References Cited

U.S. PATENT DOCUMENTS

| 2002/0128865 A1* | 9/2002 | Alten | 705/2 |
| 2006/0085223 A1* | 4/2006 | Anderson et al. | 705/2 |
| 2006/0173725 A1* | 8/2006 | Abraham et al. | 705/8 |

OTHER PUBLICATIONS

Allergenic Fractions of Alternaria SP by Le Beau, Leon Joseph, University of Illinois at Chicago, Health Sciences Center, 1952. Retrieved from ProQuest Dissertations and Theses. 0007298; http://search.proquest.com/docview/302039007?accountid=14753.*

* cited by examiner

*Primary Examiner* — Gerald J. O'Connor
*Assistant Examiner* — Mark Holcomb
(74) *Attorney, Agent, or Firm* — Schiff Hardin LLP

(57) ABSTRACT

The present invention relates generally to a method of displaying which treatment plan is administered at each fraction of a complete radiotherapy treatment, comprising displaying treatment plans $P_1$ through $P_n$, receiving an input that designates which plan or multiple plans from plans $P_1$ through $P_n$ will be administered for each treatment day $T_1$ through $T_m$, and receiving an input that designates an order of administration of the treatment plans for each treatment day $T_1$ through $T_m$. This method also includes linking the designated treatment plans with the designated treatment days $T_1$ through $T_m$, displaying the links as treatment fractions, displaying the treatment fractions in a sequential order, providing a function that sums the designated treatment plans for each treatment day $T_1$ through $T_m$, providing a component for exchanging the designated treatment plans, providing a component for removing or changing the order of administration, providing a component for approving the fractions and the order of administration, and preventing changes of the fractions and changes of the order of administration after an approval is received.

14 Claims, 4 Drawing Sheets

FRACTION SEQUENCE CONCEPT FOR RADIATION THERAPY PLANNING

CROSS REFERENCE TO RELATED APPLICATIONS

The present application claims the benefit of U.S. Provisional Application No. 60/909,063, filed Mar. 30, 2007, herein incorporated by reference.

BACKGROUND

The present invention relates generally to a method for displaying radiotherapy treatment plans.

About fifty or sixty percent of patients with cancer require radiation at sometime during their lifetime. Basically two types of radiation treatment exist: external radiation and brachytherapy, or radiation at a short distance. However, other types of radiation therapy (RT) may exist depending on the type of cancer and patient involved in the radiation treatment.

Radiation therapy in the great majority of cases is done in fractions. The therapeutic dose is administered once or several times a day, and distributed over many sessions (fractions). The dose depends primarily on tumor type, but the doctor considers many other factors including whether radiation is given alone or with chemotherapy, whether radiation is given before or after surgery, and the success of surgery and its findings. Moreover, the radiation therapy may involve several targets that require different total doses depending on these factors.

In some instances, for a single target, the fractions are identical in terms of the radiation technique used and dosage applied. However, in other instances, the fractions use different radiation techniques and different dosages at different times for a single target, or multiple targets.

The typical fractionation schedule is 1.8 to 2 grays (Gy) per fraction, with one fraction per day. The typical treatment schedule is five days per week, no weekends. Alternative fractionation schedules also exist. One of the best known is the Continuous Hyperfractionated Accelerated Radio-Therapy (CHART) regimen for lung cancer, which uses three smaller fractions per day in the treatment of lung cancer, including weekends. Twice-a-day treatments have also been tried for other sites, such as head and neck cancers. One specific twice-a-day therapy is the boost regimen. With the boost technique, a second fraction is added to "boost" the gross disease during the final approximate two weeks of treatment.

The radiation technique used during one fraction is developed in the form of a treatment (Tx) plan with the aid of a treatment planning system ("TPS"). Such a Tx plan is then made available for the radiation treatment. Specifically, a Tx plan contains geometric and dosimetric data that specifies a course of external beam and/or brachytherapy treatment, such as beam angles, collimator openings, beam modifiers, and brachytherapy channel and source specifications. If not all the fractions involve the same Tx plan, multiple plans are prepared that usually, depending on the fraction number, are added together by the TPS, so that the cumulative therapeutic effect can be assessed from the total dosage distribution.

The goal of treatment planning is to create the best Tx plan for each target. To do so, many plans are created, some of which will never be used. The doctor must choose the best plan, and create the best combination of plans to treat the target(s).

However, current treatment planning systems do not adequately determine the order of executing the various Tx plans. The Digital Imaging and Communications in Medicine (DICOM) RT standard uses a "fraction pattern" concept to determine such order. However, the timing information cannot at present be reproduced adequately. Further, DICOM RT uses the "fraction pattern" concept in a rigid timing scheme.

To solve this problem, the Tx plans generated by a TPS and issued for therapy are exported individually to a so-called "oncology information system" (OIS), where they are sorted "by hand" into correct order in a scheduler. Such a system fails to provide the graphical tools necessary to oversee the consequences of putting Tx plans into the incorrect treatment order. The dosimetrist responsible for selecting the correct Tx plans within the OIS may quite easily put such plans in the wrong order. With this system, errors can only be avoided by adding a time consuming quality control process. Further, it creates a tedious process when various radiation modalities must be mixed with one another.

The inventors have recognized a problem with the current treatment planning systems and methods of ordering Tx plans by an oncology information system. Such systems do not adequately and efficiently determine the order of executing the various Tx plans that may be required to effectively treat a patient, and do not adequately display such information to the user.

SUMMARY

The present invention according to one embodiment relates generally to a method of displaying which treatment plan is administered at each fraction of a complete radiotherapy treatment, comprising: receiving an input that designates which plan or multiple plans from plans $P_1$ through $P_n$ will be administered for each treatment day $T_1$ through $T_m$; receiving an input that designates an order of administration of the treatment plans for each treatment day $T_1$ through $T_m$; linking the designated treatment plans with the designated treatment days $T_1$ through $T_m$; displaying the links as treatment fractions; displaying the treatment fractions in a sequential order; providing a function that sums the designated treatment plans for each treatment day $T_1$ through $T_m$; providing a component for exchanging the designated treatment plans; providing a component for removing or changing the order of administration; providing a component for approving the fractions and the order of administration; and preventing changes of the fractions and changes of the order of administration after an approval is received.

The present invention according to another embodiment relates generally to a method of utilizing a treatment planning system, comprising: designating a plan or multiple plans from treatment plans $P_1$ through $P_n$ for each treatment day $T_1$ through $T_m$; designating an order of administration of the designated treatment plans for each treatment day $T_1$ through $T_m$; inputting the designations into the treatment planning system; viewing one or more treatment fractions that link the designated treatment plans with the designated treatment days $T_1$ through $T_m$; viewing the treatment fractions in a sequential order; viewing a summation of the fractions for each treatment day $T_1$ through $T_m$; and approving the treatment fractions and the order of administration.

BRIEF DESCRIPTION OF THE DRAWINGS

The invention is described below with reference to the embodiments illustrated in the drawings and following descriptive text.

DETAILED DESCRIPTION

Figure 1:
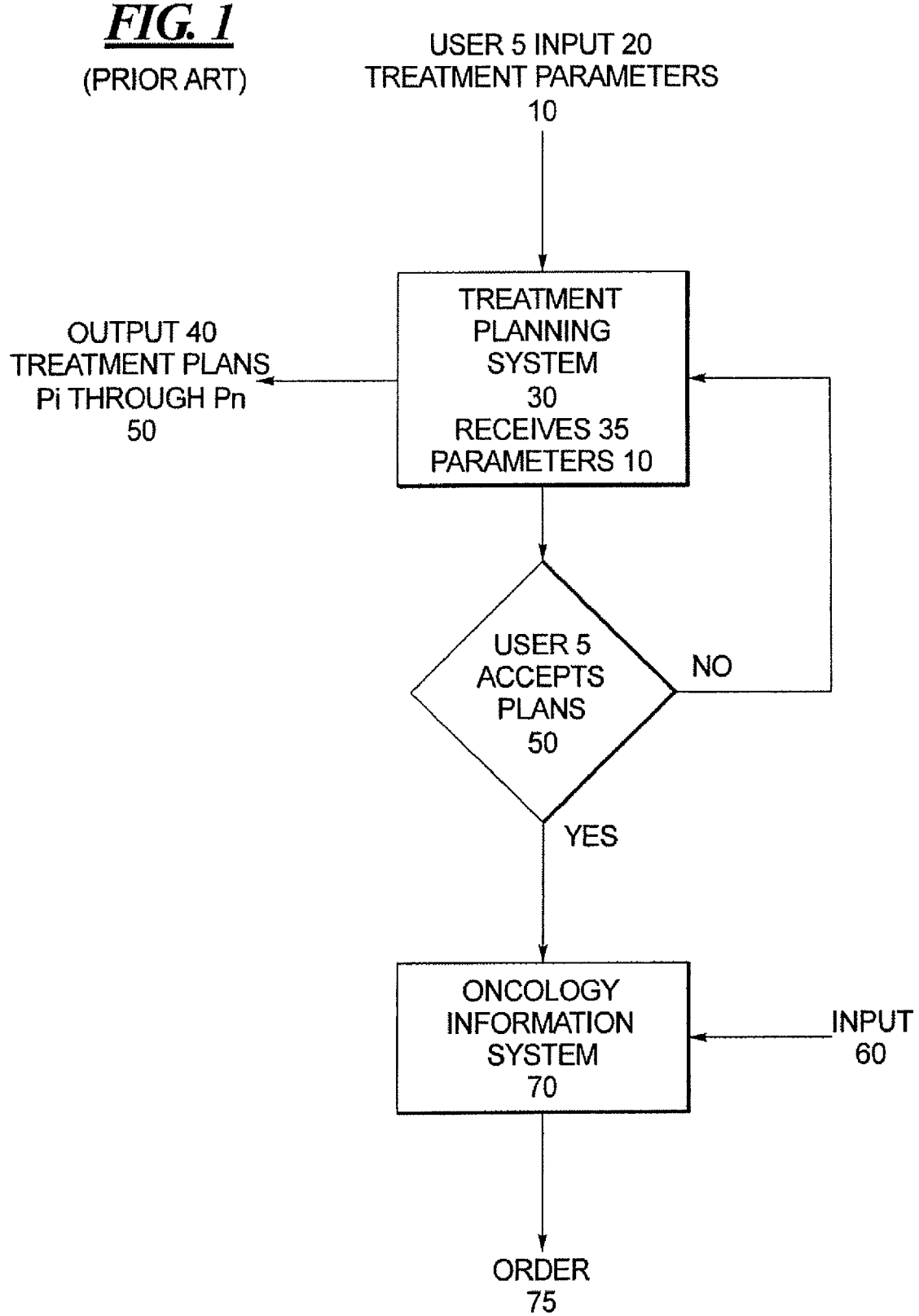
FIG. 1 is a flow chart diagram of the prior art method of creating and ordering treatment plans for radiation therapy.

As shown in FIG. 1, in the prior art, the user 5 determines one or more treatment parameters 10 that will be used to create a radiation therapy that will be administered to a patient over a set period of days. Such parameters include, but are not limited to, prescribed dose, radiation type, number of treatment beams, beam entrance directions, and beam modifiers. After determining the parameters 10, the user 5 inputs 20 the parameters 10 into a treatment planning system 30. The treatment planning system 30 may be comprised of any of the following modules: segmentation module, treatment plan definition module, dose calculation and optimization module, review and comparison module, and a reporting module.

After receiving 35 the parameters as input 20 from the user 5, the treatment planning system 30 creates a number of treatment plans $P_1$ through $P_n$ 50, and outputs 40 the treatment plans 50. The treatment plans $P_1$ through $P_n$ 50 include, but are not limited to, geometric and dosimetric data that specifies a course of external beam and/or brachytherapy treatment, such as beam angles, collimator openings, beam modifiers, and brachytherapy channel and source specifications. Moreover, treatment plans $P_1$ through $P_n$ 50 include treatment plans that will be used by the oncologist or user 5 to treat the patient, as well as treatment plans that the user 5 will not use to treat the patient. The user 5 then inputs 60 these treatment plans $P_1$ through $P_n$ 50 in a so-called "oncology information system" (OIS) 70, where the treatment plans $P_1$ through $P_n$ 50 are sorted "by hand" into the correct order 75. Such a system fails to provide the graphical tools necessary to oversee the consequences of putting Tx plans into the correct treatment order. Moreover, such a system adds a layer of confusion by outputting 40 treatment plans that the user 5 will not use to treat the patient.

Figure 2:
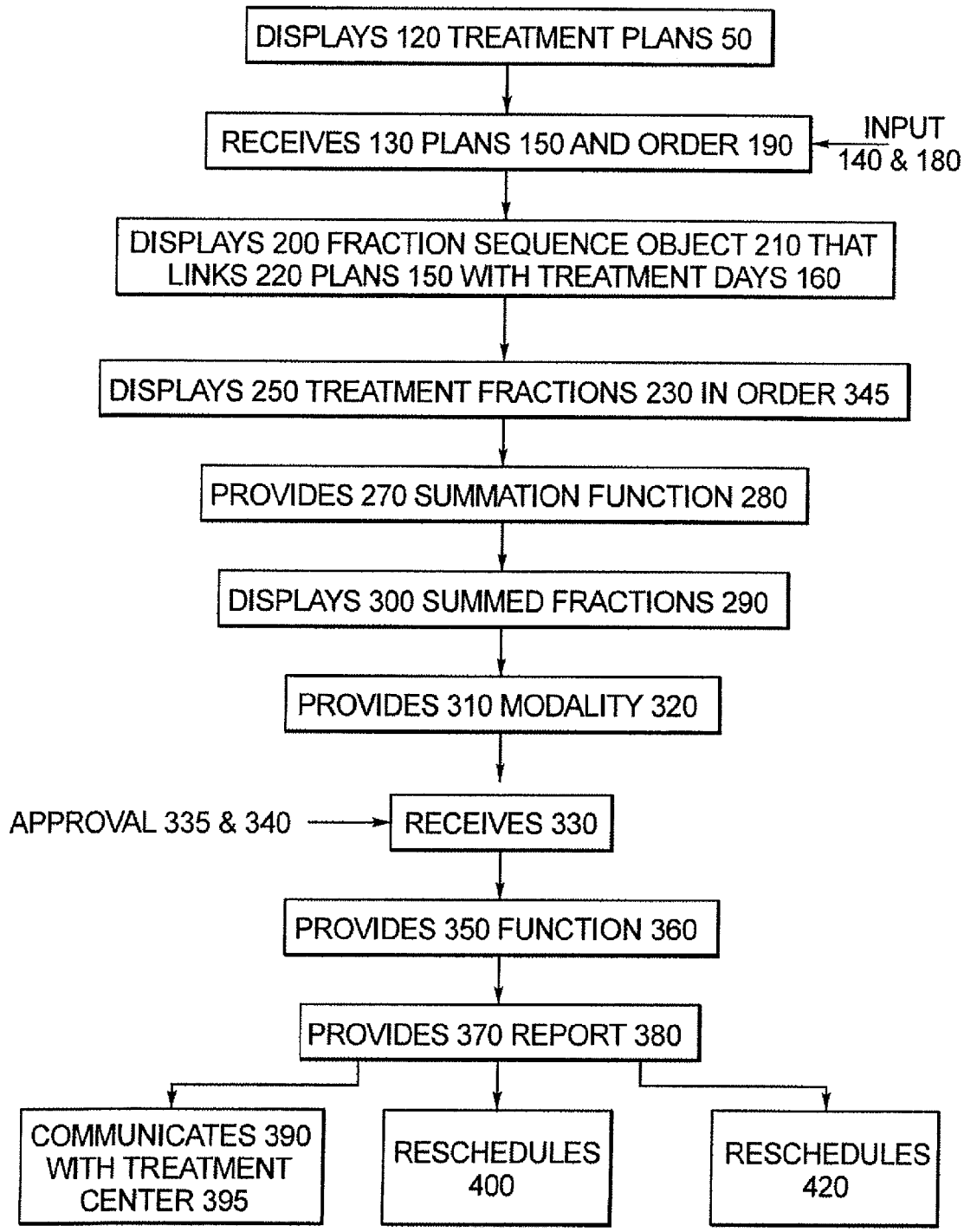
FIG. 2 is a flow chart diagram of the method of displaying which treatment plan is administered at each fraction of a complete radiotherapy treatment.
Figure 4:
FIG. 4 is a front view of a screen shot of the treatment planning system and its components used by the present invention.

An exemplary embodiment of the present invention solves this problem by providing a method of displaying which treatment plan is administered at each fraction of a complete radiotherapy treatment, and providing a report that only includes treatment plans that the user 5 will use to treat the patient. As shown in FIG. 1, the method includes a first step of receiving 35 parameters 10 for treatment as input 20 from a user 5. The method then outputs 40 treatment plans $P_1$ through $P_n$ 50 that are based on the parameters 10. As shown in FIG. 2 and FIG. 4, these treatment plans $P_1$ through $P_n$ 50 are then displayed 120 to a user 5. The method then receives 130 input 140 from a user 5 that designates which plan or multiple plans 150 from treatment plans $P_1$ through $P_n$ 50 will be administered for each treatment day $T_1$ through $T_m$ 160. In one embodiment of the present invention, treatment days $T_1$ through $T_m$ 160 are limited to days on which treatment is administered.

At the same time, the exemplary embodiment of the present invention shown in FIG. 2 and FIG. 4 also receives 130 input 180 from a user 5 that designates the order 190 that treatment plans 150 will be administered for each treatment day $T_1$ through $T_m$ 160. The method then displays 200 the chosen treatment plans 150 in a fraction sequence object 210 that links 220 the treatment plans 150 with the treatment days $T_1$ through $T_m$ 160 on which each treatment plan 150 will be administered. These "links" are displayed as treatment fractions 230.

In one embodiment, the number of treatment fractions 230 per treatment day $T_1$ through $T_m$ 160 is greater than one. In another embodiment of the present invention, the maximum number of treatment fractions 230 per treatment day $T_1$ through $T_m$ 160 is one. In an alternative embodiment of the present invention, the maximum number of treatment fractions 230 per treatment day $T_1$ through $T_m$ 160 is greater than or equal to one.

Moreover, as shown in FIG. 4, in an embodiment of the present invention, the fraction sequence object 210 is comprised of a matrix 240. In one embodiment, the matrix 240 is three-dimensional.

As shown in FIG. 2 and FIG. 4, the method then displays 250 the fractions 230 in an order of administration 345 for each treatment day $T_1$ through $T_m$ 160. The method also provides 270 a function 280 that sums the treatment fractions 230 for each treatment day $T_1$ through $T_m$ 160 into summed fractions 290, and displays 300 the summed fractions 290 to the user 5. The method then provides 310 a modality 320 that allows the user to exchange a treatment plan for any fraction with an alternative treatment plan for each treatment day $T_1$ through $T_m$ 160. Once the user decides that its designated treatment plans 150 are correct for each treatment day $T_1$ through $T_m$ 160, the method then receives 330 an approval 335 of the treatment fractions 230 and an approval 340 of the order of administration 345 from the user 5. The method then provides 350 a function 360 that prevents the user from changing the treatment fractions 230 and the order of administration 345 after the approval is received 330 from the user 5. The method then provides 370 a report 380 that includes those treatment plans 150 chosen by the user 5 to treat the patient, and the chosen order of administration 345.

In an embodiment of the present invention, the method of displaying which treatment plan is administered at each fraction of a complete radiotherapy treatment includes a further step of communicating 390 the treatment fractions 230 for each treatment day $T_1$ through $T_m$ 160 to a treatment center 395, as shown in FIG. 2. In another embodiment of the present invention, the method of displaying which treatment plan is administered at each fraction of a complete radiotherapy treatment includes an additional step of rescheduling 400 one or more treatment plans from treatment plans 150 that remain(s) after a missed treatment.

Moreover, sometimes a treatment fraction 230 is interrupted for any number of reasons. In an embodiment of the present invention, the method of displaying which treatment plan is administered at each fraction of a complete radiotherapy treatment includes a further step of automatically rescheduling 420 the interrupted treatment fraction for the next treatment day 160, so that the interrupted treatment fraction is not missed but rather re-administered in the correct order of administration 345.

Another exemplary embodiment of the present invention includes a method of utilizing a treatment planning system that displays which treatment plan is administered at each fraction of a complete radiotherapy treatment. As shown in FIG. 1, such method includes a first step whereby the user 5 inputs 20 parameters 10 for treatment into a treatment planning system 30. After the treatment planning system 30 creates treatment plans $P_1$ through $P_n$ 50, the user 5 receives the treatment plans $P_1$ through $P_n$ 50 as an output 40 from the treatment planning system 30. In this exemplary embodiment, the treatment plans $P_1$ through $P_n$ 50 received by the user 5 are based on the parameters 10 input 20 by the user 5.

Figure 3:
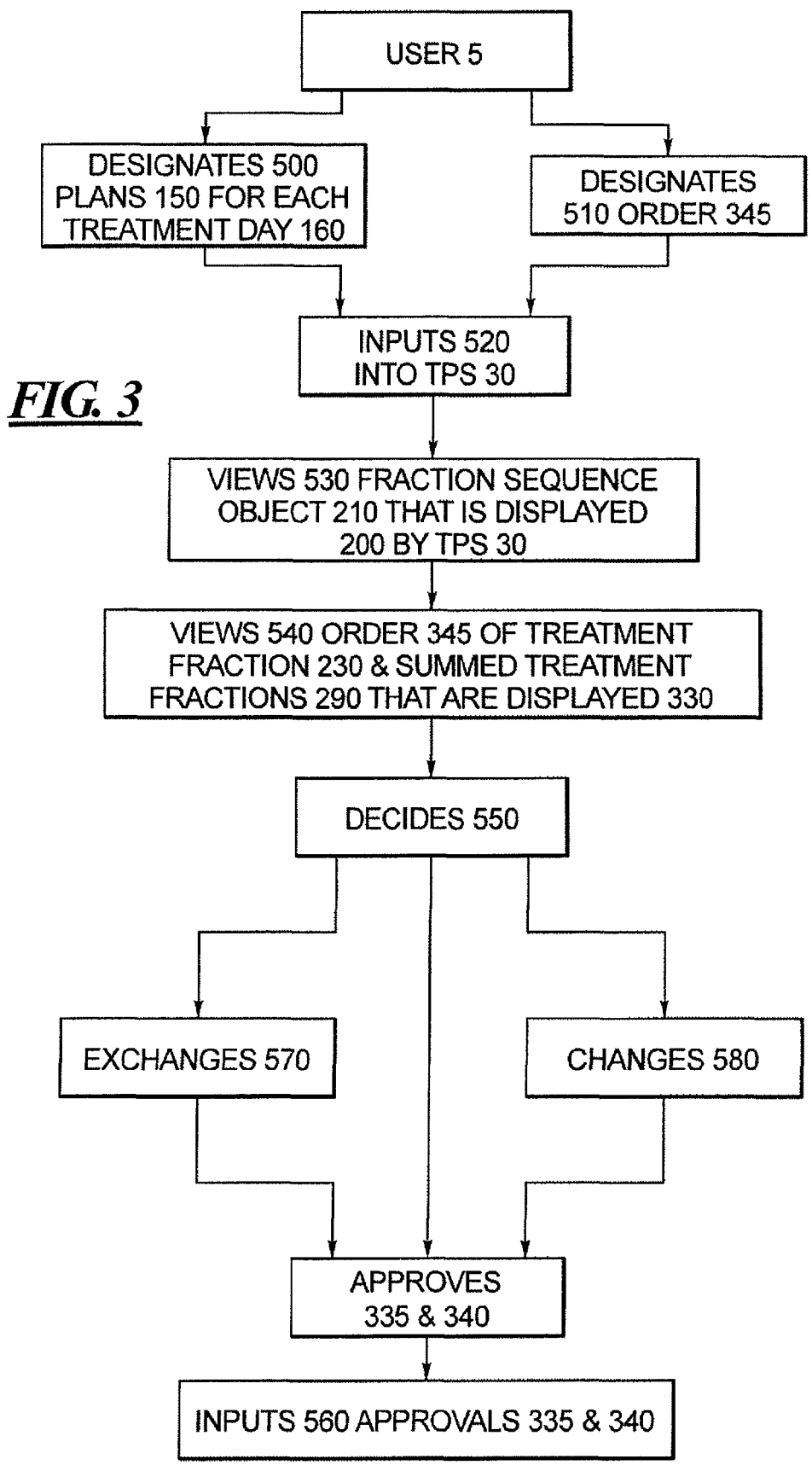
FIG. 3 is a flow chart diagram of the method of utilizing a treatment planning system.

Once received, as shown in FIG. 3, the user 5 designates 500 a plan or multiple plans 150 from treatment plans $P_1$ through $P_n$ 50 for each treatment day $T_1$ through $T_m$ 160. The user 5 also designates 510 the order 345 that each designated treatment plan 150 will be administered for each treatment day $T_1$ through $T_m$ 160. Once the user 5 makes these designations, the user 5 then inputs 520 the designated treatment plans 150 and the order of administration 345 into the treatment planning system 30.

As shown in FIG. 3, the user 5 then views 530 the fraction sequence object 210 that is displayed 200 by the treatment planning system 30. Fraction sequence object 210 links 220 the designated treatment plans 150 with the treatment days $T_1$ through $T_m$ 160 on which each treatment plan 150 will be administered as treatment fractions 230. In one embodiment of the present invention, treatment days $T_1$ through $T_m$ 160 are limited to days on which treatment is administered.

As shown in FIG. 3, the user 5, via the fraction sequence object 210, also views 540 the order 345 that each treatment fraction 230 will be administered for each treatment day $T_1$ through $T_m$ 160. The user 5 also views 540 the summed treatment fractions 290 that are displayed 330 to the user 5 by the treatment planning system 30. Once the user decides 550 that its designated treatment plans 150 are correct for each treatment day $T_1$ through $T_m$ 160, as shown in FIG. 3, the user 5 then approves 335 the treatment fractions 230 and approves 340 the order of administration 345 and inputs 560 the approval(s) 335 and 340 into the treatment planning system 30.

In one embodiment of the present invention, as shown in FIG. 3, the method of utilizing a treatment planning system that displays which treatment plan is administered at each fraction of a complete radiotherapy treatment includes a further step of exchanging 570 the designated treatment plans 150 with one or more alternative treatment plan(s) for each treatment day $T_1$ through $T_m$ 160.

In another embodiment of the present invention, the method of utilizing a treatment planning system that displays which treatment plan is administered at each fraction of a complete radiotherapy treatment includes a further step of changing 580 the order of administration 345 of the treatment fractions 230 for each treatment day $T_1$ through $T_m$ 160.

FIG. 4 is another exemplary embodiment of the present invention. As shown in FIG. 4, the present invention includes a treatment planning system 30 that creates treatment plans $P_1$ through $P_n$ 50 that are available for treatment. Such treatment plans $P_1$ through $P_n$ 50 are displayed 120 to the user 5 on a display screen 600. The user 5 designates 500 which treatment plans 150 with which to treat the patient on each treatment day $T_1$ through $T_m$ 160, and inputs 520 such treatment plans 150 via a modality 610 provided by the treatment planning system 30 into the fraction sequence object 210. As shown in FIG. 4, in an exemplary embodiment of the present invention, the fraction sequence object 210 is comprised of a matrix 240 that links 220 the designated treatment plans 150 with each treatment day $T_1$ through $T_m$ 160. In this exemplary embodiment, each "link" constitutes one square in the matrix 240. However, other designations could be used to designate which treatment plans 150 are used on which treatment days $T_1$ through $T_m$ 160. Moreover, the fraction sequence object 210, as shown in FIG. 4, also displays 250 the order 345 that each treatment plan 150 is administered on each treatment day $T_1$ through $T_m$ 160. In the example shown in FIG. 4, two treatment fractions 230 are administered per treatment day $T_1$ through $T_m$ 160. Plan A is administered first as the first treatment fraction on Day 3, and then Plan A and B are co-administered together as the second treatment fraction on Day 3. On Day 4, Plan A and C are co-administered as the first treatment fraction, and then Plan C is subsequently administered as the second treatment fraction on Day 4.

For the purposes of promoting an understanding of the principles of the invention, reference has been made to the embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of computer hardware and/or computer software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using computer software programming or software element, the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method of utilizing a treatment planning system having a computer to design in a planning process and deliver one or more treatment plans for a complete radiotherapy treatment, comprising:

designating to the computer a plan or multiple plans from treatment plans $P_1$ through $P_n$ for each treatment day $T_1$ through $T_m$;

designating to the computer an order of administration of the designated treatment plans for each treatment day $T_1$ through $T_m$;

inputting to the computer the designations into the treatment planning system;

viewing on a computer display one or more treatment fractions that link the designated treatment plans with the designated treatment days $T_1$ through $T_m$;

viewing on the computer display the treatment fractions in a sequential order;

viewing on the computer display a summation of the fractions for each treatment day $T_1$ through $T_m$;

at an end of the planning process approving with the computer the treatment fractions and the order of administration; and after the approval at the end of the planning process and before any patient treatment with the treatment plans conveying the treatment plans to a treatment center and preventing with the computer changes of the treatment fractions and order of administration after the approval is received.

2. The method of claim 1, further comprising during said planning process changing the treatment plans for one or more of the treatment days $T_1$ through $T_m$.

3. The method of claim 2, further comprising during said planning process changing the order of administration of the treatment fractions.

4. The method of claim 1, further comprising during said planning process changing the order of administration of the treatment fractions.

5. The method of claim 1, wherein a maximum number of fractions per treatment day $T_1$ through $T_m$ is greater than one.

6. The method of claim 1, wherein a maximum number of fractions per treatment day $T_1$ through $T_m$ is one.

7. The method of claim 1, wherein the links comprise a matrix.

8. The method of claim 1, further comprising receiving a report that includes the treatment fractions and the order of administration.

9. A method of displaying in a planning process which treatment plan is administered at each fraction of a complete radiotherapy treatment and then conveying the plans to a treatment center, comprising:

for the planning process displaying treatment plans $P_1$ through $P_n$ on a display of a treatment planning system computer;

receiving an input at the computer that designates which plan or multiple plans from plans $P_1$ through $P_n$ will be administered for each treatment day $T_1$ through $T_m$;

receiving an input at the computer that designates an order of administration of the treatment plans for each treatment day $T_1$ through $T_m$;

linking with the computer the designated treatment plans with the designated treatment days $T_1$ through $T_m$;

displaying on the computer display the links as treatment fractions;

displaying on the computer display the treatment fractions in a sequential order;

providing in the computer a function that sums the designated treatment plans for each treatment day $T_1$ through $T_m$;

providing in the computer a component for exchanging the designated treatment plans;

providing in the computer a component for removing or changing the order of administration;

at an end of the planning process providing in the computer a component for approving the fractions and the order of administration; and after the approval at the end of the planning process and before any patient treatment with the plans conveying the plans to the treatment center and preventing with the computer changes of the fractions and changes of the order of administration after the approval is received.

10. The method of claim 9, wherein the treatment days $T_1$ through $T_m$ are limited to days on which treatment is administered.

11. The method of claim 9, wherein a maximum number of fractions per treatment day $T_1$ through $T_m$ is greater than one.

12. The method of claim 9, wherein a maximum number of fractions per treatment day $T_1$ through $T_m$ is one.

13. The method of claim 9, wherein the links comprise a matrix.

14. The method of claim 9, further comprising providing a report that includes the fractions and the order of administration.

* * * * *